United States Patent
Jones et al.

(10) Patent No.: US 12,172,999 B2
(45) Date of Patent: Dec. 24, 2024

(54) POLYMORPHS

(71) Applicant: SYNGENTA PARTICIPATIONS AG, Basel (CH)

(72) Inventors: Ian Kevin Jones, Bracknell (GB); John Hone, Bracknell (GB); Neil George, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

(21) Appl. No.: 18/157,507

(22) Filed: Jan. 20, 2023

(65) Prior Publication Data

US 2023/0151009 A1    May 18, 2023

Related U.S. Application Data

(62) Division of application No. 16/472,719, filed as application No. PCT/EP2017/082983 on Dec. 15, 2017, now Pat. No. 11,572,361.

(30) Foreign Application Priority Data

Dec. 22, 2016  (GB) .................................... 1622006
Oct. 18, 2017  (GB) .................................... 1717104

(51) Int. Cl.
  *C07D 471/10* (2006.01)
  *A01N 43/90* (2006.01)
(52) U.S. Cl.
  CPC .......... *C07D 471/10* (2013.01); *A01N 43/90* (2013.01); *C07B 2200/13* (2013.01)
(58) Field of Classification Search
  None
  See application file for complete search history.

(56) References Cited

U.S. PATENT DOCUMENTS

| 11,001,584 B2 | 5/2021 | Jones et al. |
| 11,572,361 B2 * | 2/2023 | Jones ............... A01N 43/90 |
| 2015/0216166 A1 | 8/2015 | Koerber et al. |

FOREIGN PATENT DOCUMENTS

| WO | 2010066780 A1 | 6/2010 |
| WO | 2011151247 A2 | 12/2011 |

(Continued)

OTHER PUBLICATIONS

M.R. Caira et al., "Crystalline Polymorphism of Organic Compounds", Topics in Current Chemistry vol. 198, p. 164-208, 1998.

(Continued)

*Primary Examiner* — Alton N Pryor
(74) *Attorney, Agent, or Firm* — BakerHostetler; Toni-Junell Herbert

(57) ABSTRACT

The present invention relates to solid forms of the insecticide of formula (I):

(Continued)

compositions comprising the solid forms and methods of their use as insecticides.

13 Claims, 6 Drawing Sheets

(56) References Cited

FOREIGN PATENT DOCUMENTS

| WO | 2011151248 A1 | 12/2011 |
|---|---|---|
| WO | 2011151249 A2 | 12/2011 |
| WO | 2013079564 A2 | 6/2013 |
| WO | 2013107793 A2 | 7/2013 |
| WO | 2013107794 A2 | 7/2013 |
| WO | 2013107795 A2 | 7/2013 |
| WO | 2013107796 A2 | 7/2013 |
| WO | 2014187846 A1 | 11/2014 |
| WO | 2014187847 A1 | 11/2014 |
| WO | 2014191271 A1 | 12/2014 |
| WO | 2015007640 A1 | 1/2015 |

OTHER PUBLICATIONS

International Search Report for International Patent Application No. PCT/EP2017/082983 mailed on Mar. 7, 2018.

* cited by examiner

POLYMORPHS

This application is a division of U.S. application Ser. No. 16/472,719, filed Jun. 21, 2019, which is a 371 National Stage Application of International Application No. PCT/EP2017/082983, filed Dec. 15, 2017, which claims priority to GB 1717104.2, filed Oct. 18, 2017, and GB 1622006.3, filed Dec. 22, 2016, the entire contents each which are incorporated by reference herein.

This invention relates to solid forms of N-alkyl amide substituted spiroheterocyclic pyrrolidine dione derivatives, compositions comprising the solid forms and methods of their use as insecticides.

WO 2010/066780 discloses that certain N-alkyl amide substituted spiroheterocyclic pyrrolidine dione derivatives have pesticidal activity, in particular, insecticidal, acaricidal, molluscicidal and nematicidal activity. In particular, a compound of formula I is disclosed:

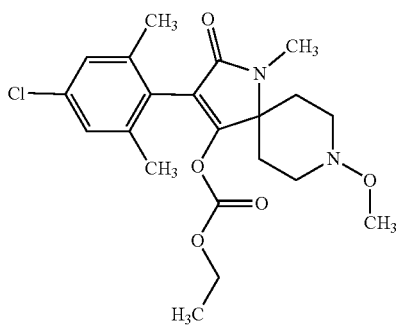

I

Mixtures of this compound with other insecticides are disclosed in WO 2013/079564, WO 2013/107793, WO 2013/107794, WO 2013/107795 and WO 2013/107796.

New solid forms of this compound, their compositions and methods of their preparation and use have now been discovered.

Accordingly, the present invention relates to novel crystalline forms of an N-alkyl amide substituted spiroheterocyclic pyrrolidine dione derivative of formula I:

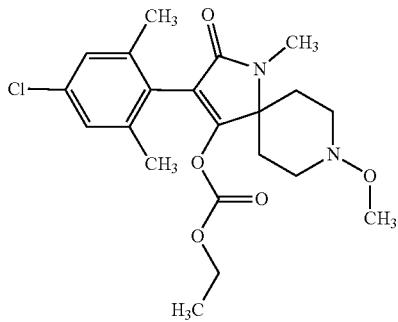

I

The crystalline polymorph of the invention may be characterised by the unit cell parameters of its single crystal as shown in Table 1. The polymorph was obtained using the method described in Example 1.

TABLE 1

| Class | Triclinic |
| --- | --- |
| Space Group | P |
| Cell Lengths (Å) | a = 8.85, b = 11.43, c = 11.96 |
| Cell Angles (°) | α = 65.26, β = 77.82, γ = 72.60 |
| Unit Cell Volume (Å$^3$) | 1043 |
| Z | 2 |

In the table, a, b, c=Length of the edges of the unit cell; α, β, γ=Angles of the unit cell; and Z=molecules per cell.

Thus, in one embodiment of the present invention, the crystalline polymorph of the invention has the following lattice parameters: a=8.85 Å±0.01 Å, b=11.43 Å±0.01 Å, c=11.96 Å±0.01 Å, α=65.26°±0.01°, β=77.82°±0.01°, γ=72.60°±0.01° and volume =1043 Å$^3$±1 Å$^3$.

The crystalline polymorph may also be characterised by a powder X-ray diffraction pattern expressed in terms of 2θ angles or d spacings. Thus, in another embodiment of the invention, the crystalline polymorph of the invention has a powder X-ray diffraction pattern comprising one 2θ angle value at 9.4±0.2, one 2θ angle value at 10.3±0.2 and at least three, at least six, at least nine, at least twelve, at least fifteen or all 2θ angle values selected from the group consisting of 8.1±0.2, 11.6±0.2, 11.9±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2. These peak values, along with the corresponding d spacing values are shown in Table 2 below:

TABLE 2

| 2-Theta | d |
| --- | --- |
| 8.1 | 10.85 |
| 9.4 | 9.94 |
| 10.3 | 8.62 |
| 11.6 | 7.65 |
| 11.9 | 7.41 |
| 13.9 | 6.38 |
| 14.8 | 5.97 |
| 16.0 | 5.55 |
| 18.2 | 4.87 |
| 18.8 | 4.71 |
| 20.4 | 4.36 |
| 20.6 | 4.30 |
| 21.2 | 4.15 |
| 21.7 | 4.10 |
| 21.9 | 4.05 |
| 22.1 | 4.01 |
| 22.4 | 3.98 |
| 23.4 | 3.79 |

These 2θ angle values are derived from a powder X-ray diffraction pattern of the polymorph that has been calculated using data from the unit cell of the single crystal. The values are generated using an average wavelength of 1.54056 Å with a 2θ step size of 0.02°.

In another embodiment, the crystalline polymorph of the invention has a melting point of 120° C.±2° C. This melting point is obtained using Differential Scanning Calorimetry (DSC) with a heating rate of 10° C./minute.

A further crystalline polymorph, named Reference Form A, may be characterised by the unit cell parameters of its single crystal as shown in Table 3. The polymorph was obtained using the method described in Example 1 and was originally disclosed in WO 2010/066780.

TABLE 3

| Class | Monoclinic |
|---|---|
| Space Group | C c |
| Cell Lengths (Å) | a = 15.92, b = 6.36, c = 22.27 |
| Cell Angles (°) | α = 90, β = 105.52, γ = 90 |
| Unit Cell Volume (Å³) | 2173 |
| Z | 4 |

In the table, a, b, c=Length of the edges of the unit cell; a, β, γ=Angles of the unit cell; and Z=molecules per cell.

The crystalline polymorph named Reference Form A, may also be characterised by a powder X-ray diffraction pattern expressed in terms of 2θ angles or d spacings. This crystalline polymorph has a powder X-ray diffraction pattern comprising 2θ angle values selected from the group consisting of 8.2±0.2, 11.5±0.2, 15.0±0.2, 15.8±0.2, 17.7±0.2, 20.2±0.2, 21.0±0.2, 21.9±0.2, 23.2±0.2 and 24.2±0.2. These peak values, along with the corresponding d spacing values are shown in Table 4 below:

TABLE 4

| 2-Theta | d |
|---|---|
| 8.2 | 10.74 |
| 11.5 | 7.66 |
| 15.0 | 5.89 |
| 15.8 | 8.26 |
| 17.7 | 4.94 |
| 20.2 | 4.33 |
| 21.0 | 4.18 |
| 21.9 | 4.02 |
| 23.2 | 3.84 |
| 24.2 | 3.65 |

These 2θ angle values are derived from a powder X-ray diffraction pattern of the polymorph that has been calculated using data from the unit cell of the single crystal. The values are generated using an average wavelength of 1.54056 Å with a 2θ step size of 0.02°.

The crystalline polymorph named Reference Form A has a melting point of 133° C. 2° C. This melting point is obtained using Differential Scanning Calorimetry (DSC) with a heating rate of 10° C./minute.

In the context of the present invention, a polymorph is a particular crystal form of a chemical compound that can exist in more than one crystal form in the solid state. A crystal form of a compound contains the constituent molecules arranged in orderly repeating patterns extending in all three spatial dimensions (in contrast, an amorphous solid form has no long-range order in the position of molecules). Different polymorphs of a compound have different arrangements of atoms and or molecules in their crystal structure. When the compound is a biologically active compound, such as an insecticide, the difference in crystal structures can lead to different polymorphs having differing chemical, physical and biological properties. Properties which may be affected include crystal shape, density, hardness, colour, chemical stability, melting point, hydroscopicity, suspensibility, dissolution rate and biological availability. As such, a specific polymorph may have properties which make it more advantageous in a particular use relative to another polymorph of the same compound: in particular, the physical, chemical and biological properties listed above can have a significant effect on the development of production methods and formulations, the ease with which a compound can be combined in a formulation with other active ingredients and formulation components and the quality and efficacy of plant treatment agents, such as insecticides. It is noted that predicting whether the solid state of a compound may be present as more than one polymorph is not possible and nor is it possible to predict the properties of any of these crystal forms.

In particular, use of a specific polymorph may allow use of new formulations compared with existing polymorphic/amorphous forms of a compound. This might be advantageous for a number of reasons. For example, a suspension concentrate (SC) formulation may be preferred over an emulsion concentrate (EC) because the lack of solvent in the SC often means that the formulation is likely to be less phytotoxic than an equivalent EC formulation—however, if the existing form of a compound is not stable in such an SC formulations, polymorphic conversion might occur leading to unwanted crystal growth. Such crystal growth is detrimental because it leads to, for example, thickening and potentially solidification of the formulation which can lead to blockages in application equipment, e.g. in spray nozzles in agricultural application machinery. Using a stable polymorphic form would overcome these issues.

Assaying the solid phase for the presence of crystals may be carried out by conventional methods known in the art. For example, it is convenient and routine to use powder X-ray diffraction techniques. Other techniques which may be used include differential scanning calorimetry (DSC), thermogravimetric analysis (TGA) and Raman or Infra-red spectroscopy, NMR, gas chromatography or HPLC. Single crystal X-ray diffraction is especially useful in identifying crystal structures.

The polymorph of the invention may be applied in unchanged form but is more preferably incorporated into agrochemical compositions by conventional means. Accordingly, in a further aspect, the invention provides an agrochemical composition comprising the polymorph of the invention as defined above and at least one agriculturally acceptable carrier or diluent.

The agrochemical compositions comprising the polymorph of the present invention are preventively and/or curatively valuable active ingredients in the field of pest control, even at low rates of application, have a favourable biocidal spectrum and are well tolerated by warm-blooded species, fish and plants. Compositions of the invention may act against all or only individual developmental stages of normally sensitive, but also resistant, animal pests, such as insects or representatives of the order *Acarina*. The insecticidal or acaricidal activity of the compositions can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

As such, the agrochemical compositions comprising the polymorph of the present invention can be used for the control of plant pathogenic insects on a number of plant species. Accordingly, the invention also provides a method of preventing or controlling insect infection on plants or plant propagation material comprising treating the plant or plant propagation material with an insecticidally effective amount of an agricultural composition of the invention.

The term "insecticide" as used herein means a compound or composition that controls or modifies the growth of insects. The term "insecticidally effective amount" means the quantity of such a compound or composition or a combination of such compounds or compositions that is capable of killing, controlling, or infecting insects, retarding the growth or reproduction of insects, reducing an insect population, and/or reducing damage to plants caused by insects.

By 'plant propagation material' is meant seeds of all kinds (fruit, tubers, bulbs, grains etc.), cuttings, cut shoots and the like.

Examples of the abovementioned animal pests are:

from the order *Acarina*, for example, *Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order *Anoplura*, for example, *Haematopinus* spp., *Linognathus* spp., *Pediculus* spp., *Pemphigus* spp. and *Phylloxera* spp.;

from the order *Coleoptera*, for example, *Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp., *Sphenophorus* spp., *Sternechus subsignatus*, *Tenebrio* spp. and *Tribolium* spp. and *Trogoderma* spp.;

from the order *Diptera*, for example, *Aedes* spp, *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example, *Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp., *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp., *Rhodnius* spp., *Sahlbergella singularis*, *Scaptocoris castanea*, *Scotinophara* spp., *Thyanta* spp, *Triatoma* spp., and *Vatiga illudens*;

from the order *Homoptera*, for example, *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aonidiella auranti*, *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp., *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, and *Zyginidia scutellaris*;

from the order *Hymenoptera*, for example, *Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order *Isoptera*, for example, *Coptotermes* spp, *Corniternes cumulans*, *Incisitermes* spp, *Macrotermes* spp, *Mastotermes* spp, *Microtermes* spp, *Reticulitermes* spp.; *Solenopsis geminate*;

from the order *Lepidoptera*, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order *Mallophaga*, for example, *Damalinea* spp. and *Trichodectes* spp.; from the order *Orthoptera*, for example, *Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order *Psocoptera*, for example, *Liposcelis* spp.;

from the order *Siphonaptera*, for example, *Ceratophyllus* spp., *Ctenocephalides* spp. and *Xenopsylla cheopis*;

from the order *Thysanoptera*, for example, *Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp; and/or from the order *Thysanura*, for example, *Lepisma saccharina*.

Examples of soil-inhabiting pests, which can damage a crop in the early stages of plant development, are:

from the order *Lepidoptera*, for example, *Acleris* spp., *Aegeria* spp., *Agrotis* spp., *Alabama argillaceae*, *Amylois* spp., *Autographa* spp., *Busseola fusca*, *Cadra cautella*, *Chilo* spp., *Crocidolomia binotalis*, *Diatraea* spp., *Diparopsis castanea*, *Elasmopalpus* spp., *Heliothis* spp., *Mamestra brassicae*, *Phthorimaea operculella*, *Plutella xylostella*, *Scirpophaga* spp., *Sesamia* spp., *Spodoptera* spp. and *Tortrix* spp.;

from the order *Coleoptera*, for example, *Agriotes* spp., *Anthonomus* spp., *Atomaria linearis*, *Chaetocnema tibialis*, *Conotrachelus* spp., *Cosmopolites* spp., *Curculio* spp., *Dermestes* spp., *Diabrotica* spp., *Dilopoderus* spp., *Epilachna* spp., *Eremnus* spp., *Heteronychus* spp., *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae*, *Sitotroga* spp., *Somaticus* spp., *Tanymecus* spp., *Tenebrio* spp., *Tribolium* spp., *Trogoderma* spp. and *Zabrus* spp.;

from the order *Orthoptera*, for example, *Gryllotalpa* spp.;

from the order *Isoptera*, for example, *Reticulitermes* spp.;

from the order *Psocoptera*, for example, *Liposcelis* spp.;

from the order *Anoplura*, for example, *Haematopinus* spp., *Linognathus* spp., *Pediculus* spp., *Pemphigus* spp. and *Phylloxera* spp.;

from the order *Homoptera*, for example, *Eriosoma larigerum*;

from the order *Hymenoptera*, for example, *Acromyrmex*, *Atta* spp., *Cephus* spp., *Lasius* spp., *Monomorium pharaonis*, *Neodiprion* spp., *Solenopsis* spp. and *Vespa* spp.; from the order *Diptera*, for example, *Tipula* spp.;

crucifer flea beetles (*Phyllotreta* spp.), root maggots (*Delia* spp.), cabbage seedpod weevil (*Ceutorhynchus* spp.) and aphids.

In particular, the compositions of the invention are particularly effective against insects from the order *Homoptera* (in particular, white flies, aphids, psyllids and armoured and soft scales), *Thysanoptera* (*thrips*) and *Acarina* (mites).

The compositions of the invention may also be useful for the control of nematodes. As such, the agrochemical compositions comprising the polymorph of the present invention can be used for the control of plant pathogenic nematodes on a number of plant species. Accordingly, the invention also provides a method of controlling damage to plant and parts thereof by plant parasitic nematodes (Endoparasitic-, Semiendoparasitic- and Ectoparasitic nematodes), the method comprising treating the plant or plant propagation material with a nematicidally effective amount of an agricultural composition of the invention.

The term "nematicide" as used herein means a compound or composition that controls or modifies the growth of nematodes. The term "nematicidally effective amount" means the quantity of such a compound or composition or a combination of such compounds or compositions that is capable of killing, controlling, or infecting nematodes, retarding the growth or reproduction of nematodes, reducing a nematode population, and/or reducing damage to plants caused by nematodes.

Examples of the abovementioned plant parasitic nematodes are:

root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina*., spp *Hypsoperine* spp., *Macroposthonia* spp., *Melinius* spp., *Punctodera* spp., and *Quinisulcius* spp.

In particular, the nematode species *Meloidogyne* spp., *Heterodera* spp., *Rotylenchus* spp. and *Pratylenchus* spp. can be controlled by the compositions of the invention.

Crops of useful plants in which the compositions according to the invention can be used include perennial and annual crops, such as berry plants for example blackberries, blueberries, cranberries, raspberries and strawberries; cereals for example barley, maize (com), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria.

Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification).

For example, a plant can have the ability to express an insecticidal protein while at the same time being herbicide tolerant, for example Herculex I® (Dow AgroSciences, Pioneer Hi-Bred International).

The rate at which the agrochemical compositions of the invention are applied will depend upon the particular type of insect etc. to be controlled, the degree of control required and the timing and method of application and can be readily determined by the person skilled in the art. In general, the compositions of the invention can be applied at an application rate of between 0.005 kilograms/hectare (kg/ha) and about 5.0 kg/ha, based on the total amount of active ingredient (wherein 'active ingredient' means the polymorph of the invention) in the composition. An application rate of between about 0.1 kg/ha and about 1.5 kg/ha is preferred, with an application rate of between about 0.3 kg/ha and 0.8 kg/ha being especially preferred.

In practice, the agrochemical compositions comprising the polymorph of the invention are applied as a formulation containing the various adjuvants and carriers known to or used in the industry.

These formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the polymorph ('active ingredient') with the formulation adjuvants in order to obtain formulations in the form of finely divided solids, granules, solutions, dispersions or emulsions. The active ingredient can also be formulated with other adjuvants, such as finely divided solids, mineral oils, oils of vegetable or animal origin, modified oils of vegetable or animal origin, organic solvents, water, surface-active substances or combinations thereof.

The active ingredient can also be contained in very fine microcapsules. Microcapsules contain the active ingredient in a porous carrier. This enables the active ingredient to be released into the environment in controlled amounts (e.g. slow-release). Microcapsules usually have a diameter of from 0.1 to 500 microns. They contain the active ingredient in an amount of about from 25 to 95% by weight of the capsule weight. The active ingredient can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the formulations according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the formulations according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive formulations generally comprise from 0.1 to 99% by weight, especially from 0.1 to 95% by weight, of polymorphs of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95% preferably 60 to 90%
surface-active agent: 1 to 30% preferably 5 to 20%
liquid carrier: 1 to 80% preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90% preferably 1 to 80%
surface-active agent: 0.5 to 20% preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%
The following Examples further illustrate, but do not limit, the invention.

| Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredient | 25% | 50% | 75% |
| light mineral oil | 5% | 5% | 5% |
| highly dispersed silicic acid | 5% | 5% | — |
| Kaolin | 6% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| active ingredient | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| active ingredient | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredient | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the active ingredient are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredient. The medium capsule diameter is 8-15 microns. The resulting formulation is applied to seeds as an aqueous suspension in an apparatus suitable for that purpose.

Each of the above formulations can be prepared as a package containing the polymorph of the invention together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid formulations, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against insect infections on the plant propagation material as well as against insects occurring in the soil. Suitably, the active ingredient may be applied to plant propagation material to be protected by impregnating the plant propagation material, in particular, seeds, either with a liquid formulation of the polymorph or coating it with a solid formulation. In special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the insect pathogen.

Normally, in the management of a crop a grower would use one or more other agronomic chemicals in addition to the crystalline polymorph of the present invention. Examples of agronomic chemicals include pesticides, such as acaricides, bactericides, fungicides, herbicides, insecticides, nematicides, as well as plant nutrients and plant fertilizers.

Accordingly, the present invention provides for the use of a composition according to the present invention together with one or more pesticides, plant nutrients or plant fertilizers. The combination may also encompass specific plant traits incorporated into the plant using any means, for example conventional breeding or genetic modification.

The mixtures of the polymorph of formula I with other active substances may also have further surprising advantages which can also be described, in a wider sense, as synergistic activity. For example, better tolerance by plants, reduced phytotoxicity, insects can be controlled in their different development stages, or better behaviour relating to production, for example grinding or mixing, storage or use.

Preferred mixtures are indicated below where the polymorph of formula I according to the invention is indicated as "I":

Compositions comprising an adjuvant include I+ compounds selected from the group of substances consisting of petroleum oils.

Compositions comprising an acaricide include I+1,1-bis (4-chlorophenyl)-2-ethoxyethanol, I+2,4-dichlorophenyl benzenesulfonate, I+2-fluoro-N-methyl-N-1-naphthylacetamide, I+4-chlorophenyl phenyl sulfone, I+abamectin, I+acequinocyl, I+acetoprole, I+acrinathrin, I+aldicarb, I+aldoxycarb, I+alpha-cypermethrin, I+amidithion, I+amidoflumet, I+amidothioate, I+amiton, I+amiton hydrogen oxalate, I+amitraz, I+aramite, I+arsenous oxide, I+AVI 382, I+AZ 60541, I+azinphos-ethyl, I+azinphos-methyl, I+azobenzene, I+azocyclotin, I+azothoate, I+benomyl, I+benoxafos, I+benzoximate, I+benzyl benzoate, I+bifenazate, I+bifenthrin, I+binapacryl, I+brofenvalerate, I+bromocyclen, I+bromophos, I+bromophos-ethyl, I+bromopropylate, I+buprofezin, I+butocarboxim, I+butoxycarboxim, I+butylpyridaben, I+calcium polysulfide, I+camphechlor, I+carbanolate, I+carbaryl, I+carbofuran, I+carbophenothion, I+CGA 50'439, I+chinomethionat, I+chlorbenside, I+chlordimeform, I+chlordimeform hydrochloride, I+chlorfenapyr, I+chlorfenethol, I+chlorfenson, I+chlorfensulfide, I+chlorfenvinphos, I+chlorobenzilate, I+chloromebuform, I+chloromethiuron, I+chloropropylate, I+chlorpyrifos, I+chlorpyrifos-methyl, I+chlorthiophos, I+cinerin I, I+cinerin II, I+cinerins, I+clofentezine, I+closantel, I+coumaphos, I+crotamiton, I+crotoxyphos, I+cufraneb, I+cyanthoate, I+cyflumetofen, I+cyhalothrin, I+cyhexatin, I+cypermethrin, I+DCPM, I+DDT, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulfon, I+diafenthiuron, I+dialifos, I+diazinon, I+dichlofluanid, I+dichlorvos, I+diclipohs, I+dicofol, I+dicrotophos, I+dienochlor, I+dimefox, I+dimethoate, I+dinactin, I+dinex, I+dinex-diclexine, I+dinobuton, I+dinocap, I+dinocap-4, I+dinocap-6, I+dinocton, I+dinopenton, I+dinosulfon, I+dinoterbon, I+dioxathion, I+diphenyl sulfone, I+disulfiram, I+disulfoton, I+DNOC, I+dofenapyn, I+doramectin, I+endosulfan, I+endothion, I+EPN, I+eprinomectin, I+ethion, I+ethoate-methyl, I+etoxazole, I+etrimfos, I+fenazaflor, I+fenazaquin, I+fenbutatin oxide, I+fenothiocarb, I+fenpropathrin, I+fenpyrad, I+fenpyroximate, I+fenson, I+fentrifanil, I+fenvalerate, I+fipronil, I+fluacrypyrim, I+fluazuron, I+flubenzimine, I+flucycloxuron, I+flucythrinate, I+fluenetil, I+flufenoxuron, I+flumethrin, I+fluorbenside, I+fluvalinate, I+FMC 1137, I+formetanate, I+formetanate hydrochloride, I+formothion, I+formparanate, I+gamma-HCH, I+glyodin, I+halfenprox, I+heptenophos, I+hexadecyl cyclopropanecarboxylate, I+hexythiazox, I+iodomethane, I+isocarbophos, I+isopropyl O-(methoxyaminothiophosphoryl)salicylate, I+ivermectin, I+jasmolin I, I+jasmolin II, I+jodfenphos, I+lindane, I+lufenuron, I+malathion, I+malonoben, I+mecarbam, I+mephosfolan, I+mesulfen, I+methacrifos, I+methamidophos, I+methidathion, I+methiocarb, I+methomyl, I+methyl bromide, I+metolcarb, I+mevinphos, I+mexacarbate, I+milbemectin, I+milbemycin oxime, I+mipafox, I+monocrotophos, I+morphothion, I+moxidectin, I+naled, I+NC-184, I+NC-512, I+nifluridide, I+nikkomycins, I+nitrilacarb, I+nitrilacarb 1:1 zinc chloride complex, I+NNI-0101, I+NNI-0250, I+omethoate, I+oxamyl, I+oxydeprofos, I+oxydisulfoton, I+pp'-DDT, I+parathion, I+permethrin, I+petroleum oils, I+phenkapton, I+phenthoate, I+phorate, I+phosalone, I+phosfolan, I+phosmet, I+phosphamidon, I+phoxim, I+pirimiphos-methyl, I+poly chloroterpenes, I+polynactins, I+proclonol, I+profenofos, I+promacyl, I+propargite, I+propetamphos, I+propoxur, I+prothidathion, I+prothoate, I+pyrethrin I, I+pyrethrin II, I+pyrethrins, I+pyridaben, I+pyridaphenthion, I+pyrimidifen, I+pyrimitate, I+quinalphos, I+quintiofos, I+R-1492, I+RA-17, I+rotenone, I+schradan, I+sebufos, I+selamectin, I+SI-0009, I+sophamide, I+spirodiclofen, I+spiromesifen, I+SSI-121, I+sulfiram, I+sulfluramid, I+sulfotep, I+sulfur, I+SZI-121, I+tau-fluvalinate, I+tebufenpyrad, I+TEPP, I+terbam, I+tetrachlorvinphos, I+tetradifon, I+tetranactin, I+tetrasul, I+thiafenox, I+thiocarboxime, I+thiofanox, I+thiometon, I+thioquinox, I+thuringiensin, I+triamiphos, I+triarathene, I+triazophos, I+triazuron, I+trichlorfon, I+trifenofos, I+trinactin, I+vamidothion, I+vaniliprole and I+YI-5302.

Compositions comprising an anthelmintic include I+abamectin, I+crufomate, I+doramectin, I+emamectin, I+emamectin benzoate, I+eprinomectin, I+ivermectin, I+milbemycin oxime, I+moxidectin, I+piperazine, I+selamectin, I+spinosad and I+thiophanate.

Compositions comprising an avicide include I+chloralose, I+endrin, I+fenthion, I+pyridin-4-amine and I+strychnine.

Compositions comprising a biological control agent include I+*Adoxophyes orana* GV, I+*Agrobacterium radiobacter*, I+*Amblyseius* spp., I+*Anagrapha falcifera* NPV, I+*Anagrus atomus*, I+*Aphelinus abdominalis*, I+*Aphidius colemani*, I+*Aphidoletes aphidimyza*, I+*Autographa californica* NPV, I+*Bacillus firmus*, I+*Bacillus sphaericus* Neide, I+*Bacillus thuringiensis* Berliner, I+*Bacillus thuringiensis* subsp. aizawai, I+*Bacillus thuringiensis* subsp. israelensis, I+*Bacillus thuringiensis* subsp. japonensis, I+*Bacillus thuringiensis* subsp. kurstaki, I+*Bacillus thuringiensis* subsp. tenebrionis, I+*Beauveria bassiana*, I+*Beauveria brongniartii*, I+Chrysoperla carnea, I+*Cryptolaemus montrouzieri*, I+*Cydia pomonella* GV, I+*Dacnusa sibirica*, I+*Diglyphus isaea*, I+*Encarsia formosa*, I+*Eretmocerus eremicus*, I+*Helicoverpa zea* NPV, I+*Heterorhabditis bacteriophora* and H. megidis, I+*Hippodamia convergens*, I+*Leptomastix dactylopii*, I+*Macrolophus caliginosus*, I+*Mamestra brassicae* NPV, I+*Metaphycus helvolus*, I+*Metarhizium anisopliae* var. acridum, I+*Metarhizium anisopliae* var. anisopliae, I+*Neodiprion sertifer* NPV and N. lecontei NPV, I+Orius spp., I+Paecilomyces fumosoroseus, I+Phytoseiulus persimilis, I+Spodoptera exigua multicapsid nuclear polyhedrosis virus, I+Steinernema bibionis, I+Steinernema carpocapsae, I+Steinernema feltiae, I+Steinernema glaseri, I+Steinernema riobrave, I+Steinernema riobravis, I+Steinernema scapterisci, I+Steinernema spp., I+Trichogramma spp., I+Typhlodromus occidentalis and I+Verticillium lecanii.

Compositions comprising a soil sterilant include I+iodomethane and methyl bromide.

Compositions comprising a chemosterilant include I+apholate, I+bisazir, I+busulfan, I+diflubenzuron, I+dimatif, I+hemel, I+hempa, I+metepa, I+methiotepa, I+methyl apholate, I+morzid, I+penfluron, I+tepa, I+thiohempa, I+thiotepa, I+tretamine and I+uredepa.

Compositions comprising an insect pheromone include I+(E)-dec-5-en-1-yl acetate with (E)-dec-5-en-1-ol, I+(E)-tridec-4-en-1-yl acetate, I+(E)-6-methylhept-2-en-4-ol, I+(E,Z)-tetradeca-4,10-dien-1-yl acetate, I+(Z)-dodec-7-en-1-yl acetate, I+(Z)-hexadec-11-enal, I+(Z)-hexadec-11-en-1-yl acetate, I+(Z)-hexadec-13-en-11-yn-1-yl acetate, I+(Z)-icos-13-en-10-one, I+(Z)-tetradec-7-en-1-al, I+(Z)-tetradec-9-en-1-ol, I+(Z)-tetradec-9-en-1-yl acetate, I+(7E,9Z)-dodeca-7,9-dien-1-yl acetate, I+(9Z,11E)-tetradeca-9,11-dien-1-yl acetate, I+(9Z,12E)-tetradeca-9,12-dien-1-yl acetate, I+14-methyloctadec-1-ene, I+4-methylnonan-5-ol with 4-methylnonan-5-one, I+alpha-multistriatin, I+brevicomin, I+codlelure, I+codlemone, I+cuelure, I+disparlure, I+dodec-8-en-1-yl acetate, I+dodec-9-en-1-yl acetate, I+dodeca-8, I+10-dien-1-yl acetate, I+dominicalure, I+ethyl 4-methyloctanoate, I+eugenol, I+frontalin, I+gossyplure, I+grandlure, I+grandlure I, I+grandlure II, I+grandlure III, I+grandlure IV, I+hexalure, I+ipsdienol, I+ipsenol, I+japonilure, I+lineatin, I+litlure, I+looplure, I+medlure, I+megatomoic acid, I+methyl eugenol, I+muscalure, I+octadeca-2, 13-dien-1-yl acetate, I+octadeca-3,13-dien-1-yl acetate, I+orfralure, I+oryctalure, I+ostramone, I+siglure, I+sordidin, I+sulcatol, I+tetradec-11-en-1-yl acetate, I+trimedlure, I+trimedlure A, I+trimedlure Bi, I+trimedlure B2, I+trimedlure C and I+trunc-call.

Compositions comprising an insect repellent include I+2-(octylthio)ethanol, I+butopyronoxyl, I+butoxy(polypropylene glycol), I+dibutyl adipate, I+dibutyl phthalate, I+dibutyl succinate, I+diethyltoluamide, I+dimethyl carbate, I+dimethyl phthalate, I+ethyl hexanediol, I+hexamide, I+methoquin-butyl, I+methylneodecanamide, I+oxamate and I+picaridin.

Compositions comprising an insecticide include I+1-dichloro-1-nitroethane, I+1,1-dichloro-2,2-bis(4-ethylphenyl) ethane, I+, I+1,2-dichloropropane, I+1,2-dichloropropane with 1,3-dichloropropene, I+1-bromo-2-chloroethane, I+2,2,2-trichloro-1-(3,4-dichloro-phenyl)ethyl acetate, I+2,2-dichlorovinyl 2-ethylsulfinylethyl methyl phosphate, I+2-(1,3-dithiolan-2-yl)phenyl dimethylcarbamate, I+2-(2-butoxyethoxy)ethyl thiocyanate, I+2-(4,5-dimethyl-1,3-dioxolan-2-yl)phenyl methylcarbamate, I+2-(4-chloro-3,5-xylyloxy)ethanol, I+2-chlorovinyl diethyl phosphate, I+2-imidazolidone, I+2-isovalerylindan-1,3-dione, I+2-methyl (prop-2-ynyl)aminophenyl methylcarbamate, I+2-thiocyanatoethyl laurate, I+3-bromo-1-chloroprop-1-ene, I+3-methyl-1-phenylpyrazol-5-yl dimethylcarbamate, I+4-methyl(prop-2-ynyl)amino-3,5-xylyl methylcarbamate, I+5,5-dimethyl-3-oxocyclohex-1-enyl dimethylcarbamate, I+abamectin, I+acephate, I+acetamiprid, I+acethion, I+acetoprole, I+acrinathrin, I+acrylonitrile, I+alanycarb, I+aldicarb, I+aldoxycarb, I+aldrin, I+allethrin, I+allosamidin, I+allyxycarb, I+alpha-cypermethrin, I+alpha-ecdysone, I+aluminium phosphide, I+amidithion, I+amidothioate, I+aminocarb, I+amiton, I+amiton hydrogen oxalate, I+amitraz, I+anabasine, I+athidathion, I+AVI 382, I+AZ 60541, I+azadirachtin, I+azamethiphos, I+azinphos-ethyl, I+azinphos-methyl, I+azothoate, I+Bacillus thuringiensis delta endotoxins, I+barium hexafluorosilicate, I+barium polysulfide, I+barthrin, I+Bayer 22/190, I+Bayer 22408, I+bendiocarb, I+benfuracarb, I+bensultap, I+beta-cyfluthrin, I+beta-cypermethrin, I+bifenthrin, I+bioallethrin, I+bioallethrin S-cyclopentenyl isomer, I+bioethanomethrin, I+biopermethrin, I+bioresmethrin, I+bis(2-chloroethyl) ether, I+bistrifluron, I+borax, I+brofenvalerate, I+bromfenvinfos, I+bromocyclen, I+bromo-DDT, I+bromophos, I+bromophos-ethyl, I+bufencarb, I+buprofezin, I+butacarb, I+butathiofos, I+butocarboxim, I+butonate, I+butoxycarboxim, I+butylpyridaben, I+cadusafos, I+calcium arsenate, I+calcium cyanide, I+calcium polysulfide, I+camphechlor, I+carbanolate, I+carbaryl, I+carbofuran, I+carbon disulfide, I+carbon tetrachloride, I+carbophenothion, I+carbosulfan, I+cartap, I+cartap hydrochloride, I+cevadine, I+chlorbicyclen, I+chlordane, I+chlordecone, I+chlordimeform, I+chlordimeform hydrochloride, I+chlorethoxyfos, I+chlorfenapyr, I+chlorfenvinphos, I+chlorfluazuron, I+chlormephos, I+chloroform, I+chloropicrin, I+chlorphoxim, I+chlorprazophos, I+chlorpyrifos, I+chlorpyrifos-methyl, I+chlorthiophos, I+chromafenozide, I+cinerin I, I+cinerin II, I+cinerins, I+cis-resmethrin, I+cismethrin, I+clocythrin, I+cloethocarb, I+closantel, I+clothianidin, I+copper acetoarsenite, I+copper arsenate, I+copper oleate, I+coumaphos, I+coumithoate, I+crotamiton, I+crotoxyphos, I+crufomate, I+cryolite, I+CS 708, I+cyanofenphos, I+cyanophos, I+cyanthoate, I+cyclethrin, I+cycloprothrin, I+cyfluthrin, I+cyhalothrin, I+cypermethrin, I+cyphenothrin, I+cyromazine, I+cythioate, I+d-limonene, I+d-tetramethrin, I+DAEP, I+dazomet, I+DDT, I+decarbofuran, I+deltamethrin, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulphon, I+diafenthiuron, I+dialifos, I+diamidafos, I+diazinon, I+dicapthon, I+dichlofenthion, I+dichlorvos, I+dicliphos, I+dicresyl, I+dicrotophos, I+dicyclanil, I+dieldrin, I+diethyl 5-methylpyrazol-3-yl phosphate, I+diflubenzuron, I+dilor, I+dimefluthrin, I+dimefox, I+dimetan, I+dimethoate, I+dimethrin, I+dimethylvinphos, I+dimetilan, I+dinex, I+dinex-diclexine, I+dinoprop, I+dinosam, I+dinoseb, I+dinotefuran, I+diofenolan, I+dioxabenzofos, I+dioxacarb, I+dioxathion, I+disulfoton, I+dithicrofos, I+DNOC, I+doramectin, I+DSP, I+ecdysterone, I+EI 1642, I+emamectin, I+emamectin benzoate, I+EMPC, I+empenthrin, I+endosulfan, I+endothion, I+endrin, I+EPBP, I+EPN, I+epofenonane, I+eprinomectin, I+esfenvalerate, I+etaphos, I+ethiofencarb, I+ethion, I+ethiprole, I+ethoate-methyl, I+ethoprophos, I+ethyl formate, I+ethyl-DDD, I+ethylene dibromide, I+ethylene dichloride, I+ethylene oxide, I+etofenprox, I+etrimfos, I+EXD, I+famphur, I+fenamiphos, I+fenazaflor, I+fenchlorphos, I+fenethacarb, I+fenfluthrin, I+fenitrothion, I+fenobucarb, I+fenoxacrim, I+fenoxycarb, I+fenpirithrin, I+fenpropathrin, I+fenpyrad, I+fensulfothion, I+fenthion, I+fenthion-ethyl, I+fenvalerate, I+fipronil, I+flonicamid, I+flubendiamide, I+flucofuron, I+flucycloxuron, I+flucythrinate, I+fluenetil, I+flufenerim, I+flufenoxuron, I+flufenprox, I+flumethrin, I+fluvalinate, I+FMC 1137, I+fonofos, I+formetanate, I+formetanate hydrochloride, I+formothion, I+formparanate, I+fosmethilan, I+fospirate, I+fosthiazate, I+fosthietan, I+furathiocarb, I+furethrin, I+gamma-cyhalothrin, I+gamma-HCH, I+guazatine, I+guazatine acetates, I+GY-81, I+halfenprox, I+halofenozide, I+HCH, I+HEOD, I+heptachlor, I+heptenophos, I+heterophos, I+hexaflumuron, I+HHDN, I+hydramethylnon, I+hydrogen cyanide, I+hydroprene, I+hyquincarb, I+imidacloprid, I+imiprothrin, I+indoxacarb, I+iodomethane, I+IPSP, I+isazofos, I+isobenzan, I+isocarbophos, I+isodrin, I+isofenphos, I+isolane, I+isoprocarb, I+isopropyl O-(methoxyaminothiophosphoryl)salicylate, I+isoprothiolane, I+isothioate, I+isoxathion, I+ivermectin, I+jasmolin I, I+jasmolin II, I+jodfenphos, I+juvenile hormone I, I+juvenile hormone II, I+juvenile hormone III, I+kelevan, I+kinoprene, I+lambda-cyhalothrin, I+lead arsenate, I+lepimectin, I+leptophos, I+lindane, I+lirimfos, I+lufenuron, I+lythidathion, I+m-cumenyl methylcarbamate, I+magnesium phosphide, I+malathion, I+malonoben, I+mazidox, I+mecarbam, I+mecarphon, I+menazon, I+mephosfolan, I+mercurous chloride, I+mesulfenfos, I+metaflumizone, I+metam, I+metam-potassium, I+metam-sodium, I+methacrifos, I+methamidophos, I+methanesulfonyl fluoride, I+methidathion, I+methiocarb, I+methocrotophos, I+methomyl, I+methoprene, I+methoquin-butyl, I+methothrin, I+methoxychlor, I+methoxyfenozide, I+methyl bromide, I+methyl isothiocyanate, I+methylchloroform, I+methylene chloride, I+metofluthrin, I+metolcarb, I+metoxadiazone, I+mevinphos, I+mexacarbate, I+milbemectin, I+milbemycin oxime, I+mipafox, I+mirex, I+monocrotophos, I+morphothion, I+moxidectin, I+naftalofos, I+naled, I+naphthalene, I+NC-170, I+NC-184, I+nicotine, I+nicotine sulfate, I+nifluridide, I+nitenpyram, I+nithiazine, I+nitrilacarb, I+nitrilacarb 1:1 zinc chloride complex, I+NNI-0101, I+NNI-0250, I+nornicotine, I+novaluron, I+noviflumuron, I+O-5-dichloro-4-iodophenyl O-ethyl ethylphosphonothioate, I+O,O-diethyl O-4-methyl-2-oxo-2H-chromen-7-yl phosphorothioate, I+O,O-diethyl 0-6-methyl-2-propylpyrimidin-4-yl phosphorothioate, I+O, O, O',O'-tetrapropyl dithiopyrophosphate, I+oleic acid, I+omethoate, I+oxamyl, I+oxydemeton-methyl, I+oxydeprofos, I+oxydisulfoton, I+pp'-DDT, I+para-dichlorobenzene, I+parathion, I+parathion-methyl, I+penfluron, I+pentachlorophenol, I+pentachlorophenyl laurate, I+permethrin, I+petroleum oils, I+PH 60-38, I+phenkapton, I+phenothrin, I+phenthoate, I+phorate+TX, I+phosalone, I+phosfolan, I+phosmet, I+phosnichlor, I+phosphamidon, I+phosphine, I+phoxim, I+phoxim-methyl, I+pirimetaphos, I+pirimicarb, I+pirimiphos-ethyl, I+pirimiphos-methyl, I+polychlorodicyclopentadiene isomers, I+poly chloroterpenes, I+potassium arsenite, I+potassium thiocyanate, I+prallethrin, I+precocene I, I+precocene II, I+precocene III, I+primidophos, I+profenofos, I+profluthrin, I+promacyl, I+promecarb, I+propaphos, I+propetamphos, I+propoxur, I+prothidathion, I+prothiofos, I+prothoate, I+protrifenbute, I+pymetrozine, I+pyraclofos, I+pyrazophos, I+pyresmethrin, I+pyrethrin I, I+pyrethrin II, I+pyrethrins, I+pyridaben, I+pyridalyl, I+pyridaphenthion, I+pyrimidifen, I+pyrimitate, I+pyriproxyfen, I+quassia, I+quinalphos, I+quinalphos-methyl, I+quinothion, I+quintiofos, I+R-1492, I+rafoxanide, I+resmethrin, I+rotenone, I+RU 15525, I+RU 25475, I+ryania, I+ryanodine, I+sabadilla, I+schradan, I+sebufos, I+selamectin, I+SI-0009, I+SI-0205, I+SI-0404, I+SI-0405, I+silafluofen, I+SN 72129, I+sodium arsenite, I+sodium cyanide, I+sodium fluoride, I+sodium hexafluorosilicate, I+sodium pentachlorophenoxide, I+sodium selenate, I+sodium thiocyanate, I+sophamide, I+spinosad, I+spiromesifen, I+spirotetrmat, I+sulcofuron, I+sulcofuron-sodium, I+sulfluramid, I+sulfotep, I+sulfuryl fluoride, I+sulprofos, I+tar oils, I+tau-fluvalinate, I+tazimcarb, I+TDE, I+tebufenozide, I+tebufenpyrad, I+tebupirimfos, I+teflubenzuron, I+tefluthrin, I+temephos, I+TEPP, I+terallethrin, I+terbam, I+terbufos, I+tetrachloroethane, I+tetrachlorvinphos, I+tetramethrin, I+theta-cypermethrin, I+thiacloprid, I+thiafenox, I+thiamethoxam, I+thicrofos, I+thiocarboxime, I+thiocyclam, I+thiocyclam hydrogen oxalate, I+thiodicarb, I+thiofanox, I+thiometon, I+thionazin, I+thiosultap, I+thiosultap-sodium, I+thuringiensin, I+tolfenpyrad, I+tralomethrin, I+transfluthrin, I+transpermethrin, I+triamiphos, I+triazamate, I+triazophos, I+triazuron, I+trichlorfon, I+trichlormetaphos-3, I+trichloronat, I+trifenofos, I+triflumuron, I+trimethacarb, I+triprene, I+vamidothion, I+vaniliprole, I+veratridine, I+veratrine, I+XMC, I+xylylcarb, I+YI-5302, I+zeta-cypermethrin, I+zetamethrin, I+zinc phosphide, I+zolaprofos and ZXI 8901, I+cyantraniliprole, I+chlorantraniliprole, I+cyenopyrafen, I+cyflumetofen, I+pyrifluquinazon, I+spinetoram, I+spirotetramat, I+sulfoxaflor, I+flufiprole, I+meperfluthrin, I+tetramethylfluthrin, I+triflumezopyrim.

Compositions comprising a molluscicide include I+bis(tributyltin) oxide, I+bromoacetamide, I+calcium arsenate, I+cloethocarb, I+copper acetoarsenite, I+copper sulfate, I+fentin, I+ferric phosphate, I+metaldehyde, I+methiocarb, I+niclosamide, I+niclosamide-olamine, I+pentachlorophenol, I+sodium pentachlorophenoxide, I+tazimcarb, I+thiodicarb, I+tributyltin oxide, I+trifenmorph, I+trimethacarb, I+triphenyltin acetate and triphenyltin hydroxide, I+pyriprole.

Compositions comprising a nematicide include 1+AKD-3088, I+1,2-dibromo-3-chloropropane, I+1,2-dichloropropane, I+1,2-dichloropropane with 1,3-dichloropropene, I+1,3-dichloropropene, I+3,4-dichlorotetrahydrothiophene 1,1-dioxide, I+3-(4-chlorophenyl)-5-methylrhodanine, I+5-methyl-6-thioxo-1,3,5-thiadiazinan-3-ylacetic acid, I+6-isopentenylaminopurine, I+abamectin, I+acetoprole, I+alanycarb, I+aldicarb, I+aldoxycarb, I+AZ 60541, I+benclothiaz, I+benomyl, I+butylpyridaben, I+cadusafos, I+carbofuran, I+carbon disulfide, I+carbosulfan, I+chloropicrin, I+chlorpyrifos, I+cloethocarb, I+cytokinins, I+dazomet, I+DBCP, I+DCIP, I+diamidafos, I+dichlofenthion, I+dicliphos, I+dimethoate, I+doramectin, I+emamectin, I+emamectin benzoate, I+eprinomectin, I+ethoprophos, I+ethylene dibromide, I+fenamiphos, I+fenpyrad, I+fensulfothion, I+fosthiazate, I+fosthietan, I+furfural, I+GY-81, I+heterophos, I+iodomethane, I+isamidofos, I+isazofos, I+ivermectin, I+kinetin, I+mecarphon, I+metam, I+metam-potassium, I+metam-sodium, I+methyl bromide, I+methyl isothiocyanate, I+milbemycin oxime, I+moxidectin, I+*Myrothecium verrucaria* composition, I+NC-184, I+oxamyl, I+phorate, I+phosphamidon, I+phosphocarb, I+sebufos, I+selamectin, I+spinosad, I+terbam, I+terbufos, I+tetrachlorothiophene, I+thiafenox, I+thionazin, I+triazophos, I+triazuron, I+xylenols, I+YI-5302 and zeatin, I+fluensulfone.

Compositions comprising a synergist include I+2-(2-butoxyethoxy)ethyl piperonylate, I+5-(1,3-benzodioxol-5-yl)-3-hexylcyclohex-2-enone, I+farnesol with nerolidol, I+MB-599, I+MGK 264, I+piperonyl butoxide, I+piprotal, I+propyl isomer, I+S421, I+sesamex, I+sesasmolin and I+sulfoxide.

Compositions comprising an animal repellent include I+anthraquinone, I+chloralose, I+copper naphthenate, I+copper oxychloride, I+diazinon, I+dicyclopentadiene, I+guazatine, I+guazatine acetates, I+methiocarb, I+pyridin-4-amine, I+thiram, I+trimethacarb, I+zinc naphthenate and I+ziram.

Further compositions include I+Brofluthrinate, I+Cycloxaprid, I+Diflovidazine, I+Flometoquin, I+Fluhexafon, I+Guadipyr, I+*Plutella xylostella* Granulosis virus, I+*Cydia pomonella* Granulosis virus, I+Harpin, I+Imicyafos, I+*Heliothis virescens* Nucleopolyhedrovirus, I+*Heliothis puncti-* gera Nucleopolyhedrovirus, I+*Helicoverpa armigera* Nucleopolyhedrovirus, I+*Helicoverpa zea* Nucleopolyhedrovirus, I+*Spodoptera frugiperda* Nucleopolyhedrovirus, I+*Plutella xylostella* Nucleopolyhedrovirus, I+Pasteuria nishizawae, I+p-cymene, I+Pyflubumide, I+Pyrafluprole, I+pyrethrum, I+QRD 420, I+QRD 452, I+QRD 460, I+Terpenoid blends, I+Terpenoids, I+Tetraniliprole, and I+α-terpinene.

Composition also include mixtures of the polymorph and an active substance referenced by a code, such as I+code AE 1887196 (BSC-BX60309), I+code NNI-0745 GR, I+code IKI-3106, I+code JT-L001, I+code ZNQ-08056, I+code IPPA152201, I+code HNPC-A9908 (CAS: [660411-21-2]), I+code HNPC-A2005 (CAS: [860028-12-2]), I+code JS118, I+code ZJ0967, I+code ZJ2242, I+code JS7119 (CAS: [929545-74-4]), I+code SN-1172, I+code HNPC-A9835, I+code HNPC-A9955, I+code HNPC-A3061, I+code Chuanhua 89-1, I+code IPP-10, I+code ZJ3265, I+code JS9117, I+code SYP-9080, I+code ZJ3757, I+code ZJ4042, I+code ZJ4014, I+code ITM-121, I+code DPX-RAB55 (DKI-2301), I+code Me5382, I+code NC-515, I+code NA-89, I+code MIE-1209, I+code MCI-8007, I+code BCS-CL73507, I+code 5-1871, I+code DPX-RDS63, and I+code AKD-1193.

Whilst compositions comprising the polymorph of the invention and another insecticide etc. are explicitly disclosed above, the skilled man will appreciate that the invention extends to three-way, and further multiple combinations comprising the above two-way mixtures.

For the avoidance of doubt, even if not explicitly stated above, the mixing partners of may also be in the form of any suitable agrochemically acceptable ester or salt, as mentioned e.g. in The Pesticide Manual, Fifteenth Edition, British Crop Protection Council, 2009.

The weight ratio of the polymorph of the invention and another insecticide is generally between 1000:1 and 1:100, more preferably between 500:1 and 1:100, for example between 250:1 and 1:66, between 125:1 and 1:33, between 100:1 and 1:25, between 66:1 and 1:10, between 33:1 and 1:5 and between 8:1 and 1:3.

The compound of formula (I) in any form, including the crystalline form disclosed herein, or an insecticidal composition comprising a compound of formula (I) and another insecticidally-active ingredient as disclosed herein, may be used as an insecticide on soy bean plants, in particular for the control of insects from the order *Homoptera* (in particular, white flies, aphids, psyllids and armoured and soft scales), *Thysanoptera* (thrips) and *Acarina* (mites).

In particular, this includes transgenic soybean plants expressing toxins, for example insecticidal proteins such as delta-endotoxins, e.g. Cry1Ac (Cry1Ac Bt protein). Accordingly, this may include transgenic soybean plants comprising event MON87701 (see U.S. Pat. No. 8,049,071 and related applications and patents, as well as WO 2014/170327 A1 (eg, see paragraph [008] reference to Intacta RR2 PRO™ soybean)), event MON87751 (US. Patent Application Publication No. 2014/0373191) or event DAS-81419 (U.S. Pat. No. 8,632,978 and related applications and patents).

Other transgenic soybean plants may comprise event SYHT0H2—HPPD tolerance (U.S. Patent Application Publication No. 2014/0201860 and related applications and patents), event MON89788—glyphosate tolerance (U.S. Pat. No. 7,632,985 and related applications and patents), event MON87708—dicamba tolerance (U.S. Patent Application Publication No. US 2011/0067134 and related applications and patents), event DP-356043-5-glyphosate and ALS tolerance (U.S. Patent Application Publication No. US 2010/0184079 and related applications and patents), event A2704-12—glufosinate tolerance (U.S. Patent Application Publication No. US 2008/0320616 and related applications and patents), event DP-305423-1—ALS tolerance (U.S. Patent Application Publication No. US 2008/0312082 and related applications and patents), event A5547-127—glufosinate tolerance (U.S. Patent Application Publication No. US 2008/0196127 and related applications and patents), event DAS-40278-9—tolerance to 2,4-dichlorophenoxyacetic acid and aryloxyphenoxypropionate (see WO 2011/022469, WO 2011/022470, WO 2011/022471, and related applications and patents), event 127—ALS tolerance (WO 2010/080829 and related applications and patents), event GTS 40-3-2—glyphosate tolerance, event DAS-68416-4-2,4-dichlorophenoxyacetic acid and glufosinate tolerance, event FG72—glyphosate and isoxaflutole tolerance, event BPS-CV127-9—ALS tolerance and GU262—glufosinate tolerance or event SYHT04R-HPPD tolerance.

Such other insecticidally-active ingredients include, but are not limited to, pymetrozine, lambda-cyhalothrin, gamma-cyhalothrin, abamectin, emamectin benzoate, spinetoram, chlorantraniliprole, cyantraniliprole, thiamethoxam, sulfoxaflor, cyenopyrafen, acetamiprid, flonicamid and pirimicarb.

Under certain circumstances, compositions comprising a compound of formula (I) and another insecticidally-active ingredient as disclosed herein when used in controlling or preventing insect infection on soy bean plants (in particular any of the transgenic soybean plants as described above), may display synergistic interactions.

The compound of formula (I) in any form, including the crystalline form disclosed herein, or an insecticidal composition comprising a compound of formula (I) and another insecticidally-active ingredient as disclosed herein, may also be used as an insecticide on cotton plants, in particular for the control of insects from the order *Homoptera* (in particular, white flies, aphids, psyllids and armoured and soft scales), *Thysanoptera* (thrips) and *Acarina* (mites).

In particular, transgenic cotton events expressing useful traits which can be used in combination with a compound of formula (I), or with a compound of formula (I) and another active ingredient, include BXN10211, BXN10215, BXN10222, BXN10224, COT102, COT67B, GHB614, GHB119, LLCotton25, MON531, MON757, MON15985, MON1445, MON88913, MON1076, MON1698, MON88701, T304-40, 281-24-236, 3006-210-23, 31707, 31803, 31808, 42317, and the like. Such combinations of a compound of formula (I), or with a compound of formula (I) and another active ingredient, with cotton events expressing one or more useful traits may provide more durable yield protection, provide a resistance management strategy for target pest control, and reduce farmer inputs, saving considerable expense in time and monetary value.

Such other insecticidally-active ingredients include, but are not limited to, pymetrozine, lambda-cyhalothrin, gamma-cyhalothrin, abamectin, emamectin benzoate, spinetoram, chlorantraniliprole, cyantraniliprole, thiamethoxam, sulfoxaflor, cyenopyrafen, acetamiprid, flonicamid and pirimicarb.

Under certain circumstances, compositions comprising a compound of formula (I), or with a compound of formula (I) and another active ingredient as disclosed herein when used in controlling or preventing insect infection on cotton plants (in particular any of the transgenic cotton plants as described above), may display synergistic interactions.

The present invention will now be described by way of the following non-limiting examples and figures, wherein.

EXAMPLES

1. Preparation of Polymorphs

The compound of formula I was made according to the methods described in WO 2010/066780. This method led to the production of thin needle shaped crystals of the Reference Form A polymorph.

The polymorph of the invention was made by adding an excess of methylcyclohexane to the Reference Form A polymorph and heating the sample to 85 to 90° C. until no crystalline solids remained. The sample was then allowed to cool to room temperature and left undisturbed until crystal growth occurred. Chunky crystals were observed after 3 to 6 months—single-crystal X-ray diffraction analysis confirmed the presence of the polymorph of the invention.

2. Analysis of Polymorphs

After preparation by the methods detailed above, the samples were subject to analysis by powder X-ray diffraction and/or single crystal X-ray diffraction and/or differential scanning calorimetry (DSC).

Figure 1:
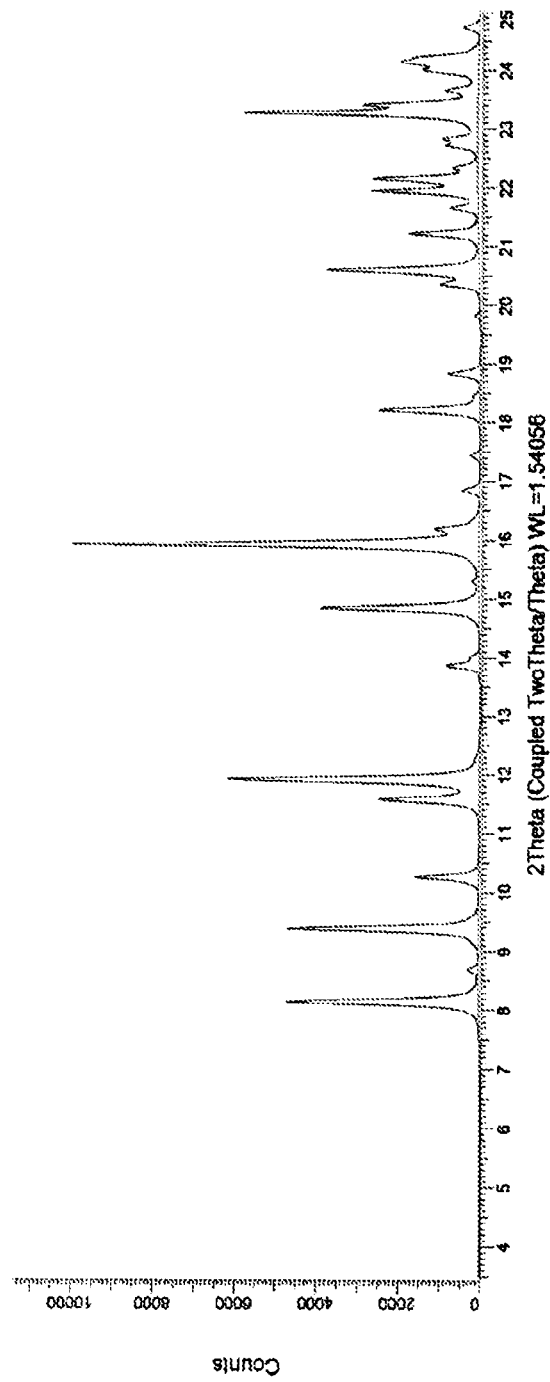
FIG. 1 shows the predicted powder X-ray diffraction pattern of the polymorph of the invention.
Figure 2:
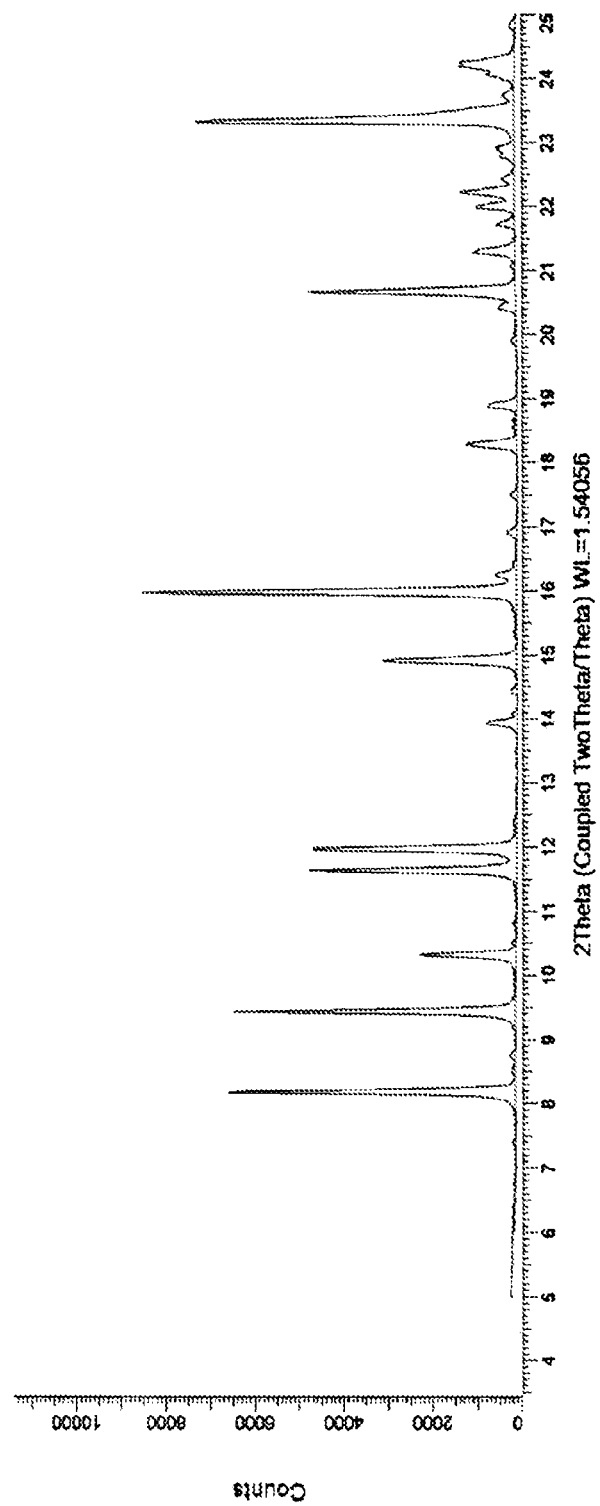
FIG. 2 shows the measured powder X-ray diffraction pattern of the polymorph of the invention.
Figure 4:
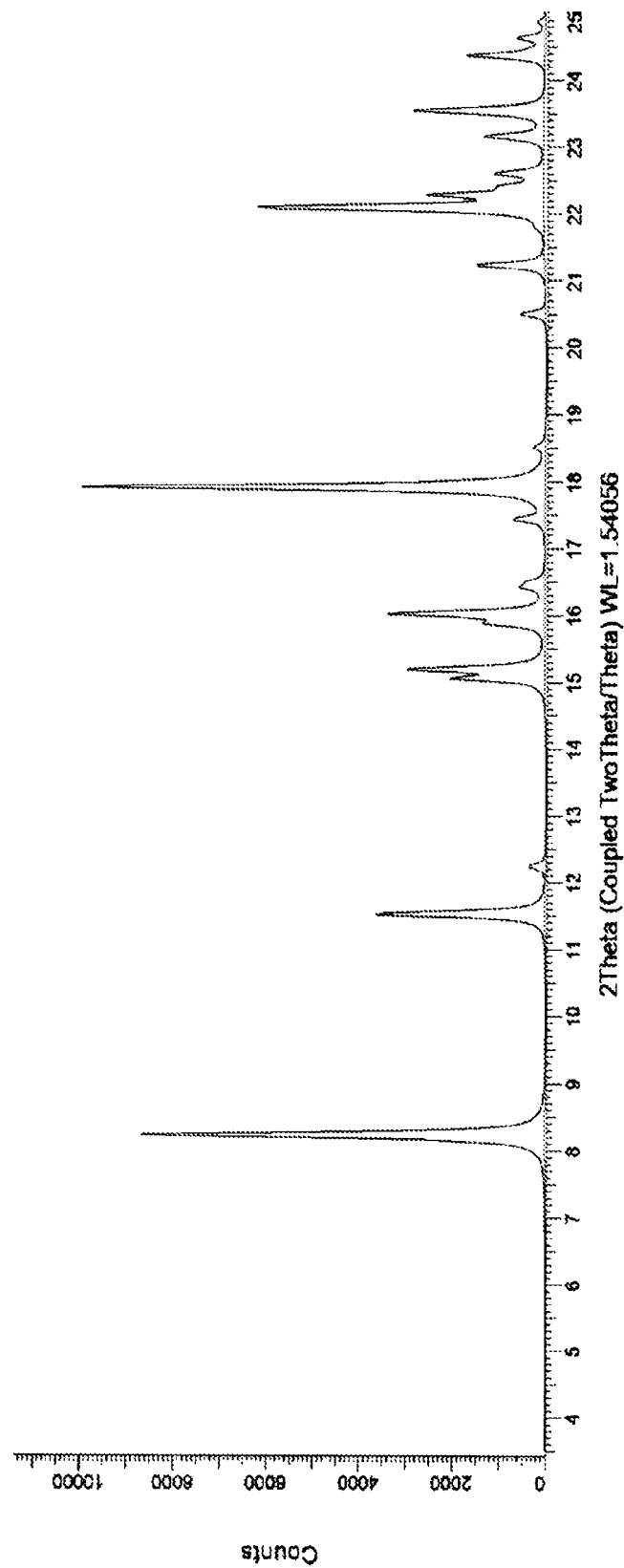
FIG. 4 shows the predicted powder X-ray diffraction pattern of the Reference Form A polymorph.
Figure 5:
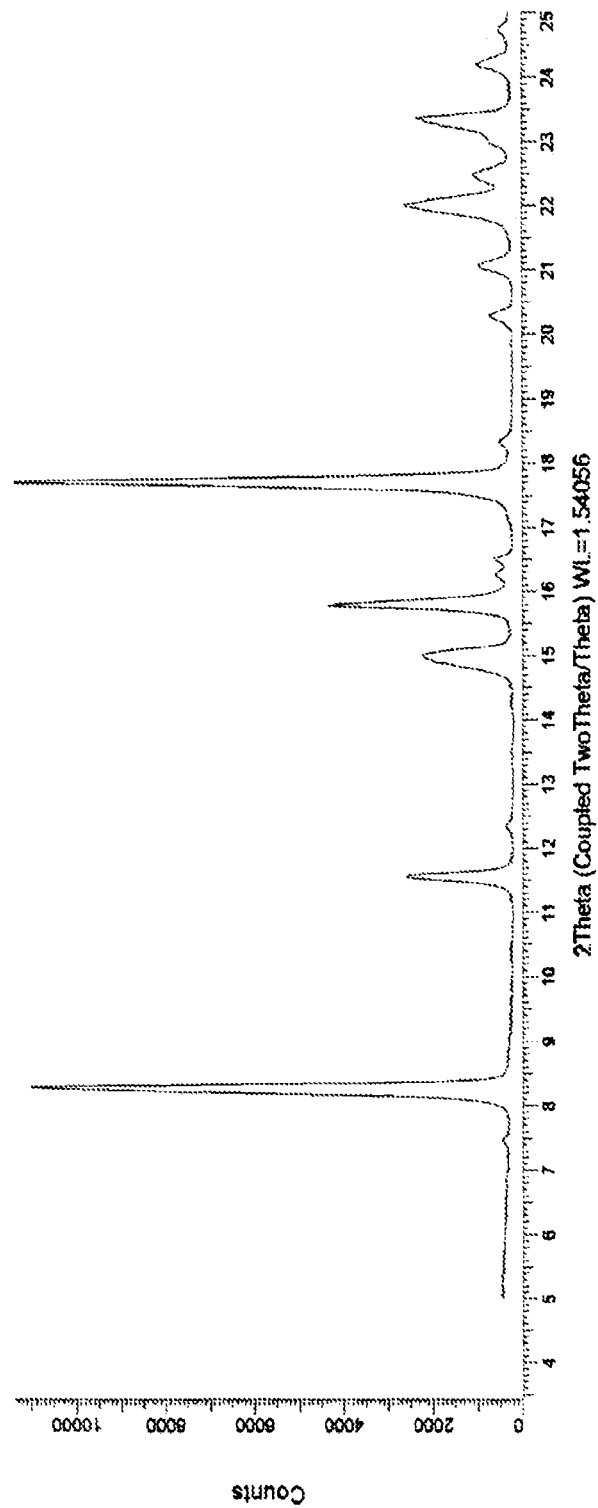
FIG. 5 shows the measured powder X-ray diffraction pattern of the of the Reference Form A polymorph.

Powder X-ray diffraction analysis of solid material was carried out using the Bruker D8 powder diffractometer at room temperature and at relative humidities above 40%. Samples were mounted in Perspex sample holders and the samples flattened. The sample holder was rotated and X-rays were collected from 4° to 34° 2-theta, with a scan time of 25 to 30 minutes depending on the pattern intensity. Measured powder X-ray diffraction patterns for the polymorph of the invention and Reference Form A are shown in FIG. 2 and FIG. 5, respectively Single crystal intensity data was collected on an Oxford Xcalibar PX Ultra diffractometer using Cu Kα radiation (λ=1.5418 Å) with a graphite monochromator. The crystal was mounted in Paratone N oil at 100K for data collection. The data was solved using the CRYSTALS software package. This data was used to produce a predicted powder X-ray diffraction pattern for the polymorph of the invention (FIG. 1) and Reference Form A (FIG. 4).

DSC was carried out using a Mettler Toledo DSC1. A sample loading of around 5 mg was used and this was heated from 25° C. to 160° C. at a rate of 10° C./minute. The lid of the DSC crucible was pierced to allow the escape of any gas formed during the heating of the sample.

Figure 3:
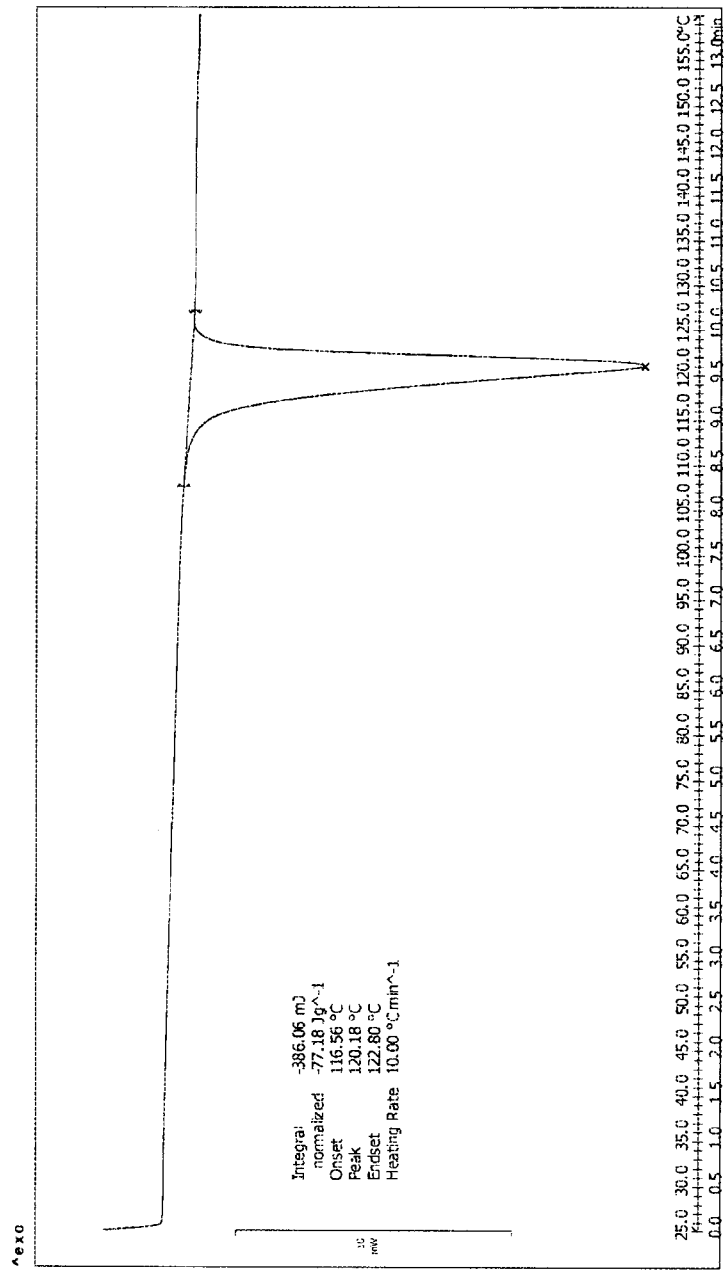
FIG. 3 shows a DSC trace of the polymorph of the invention.
Figure 6:
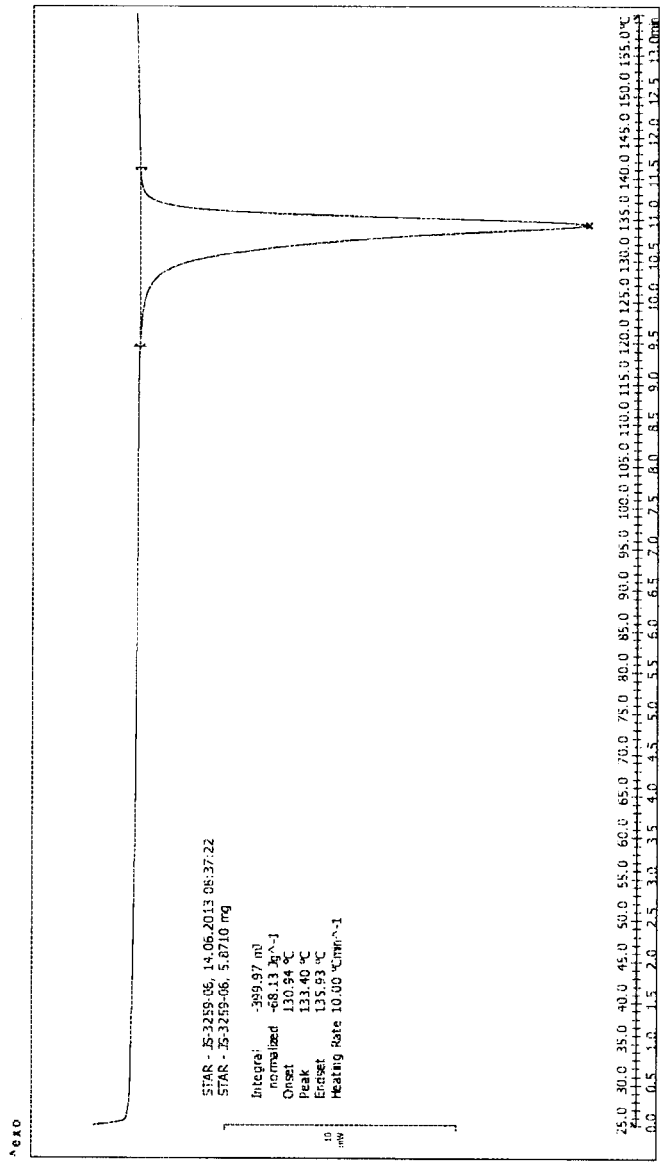
FIG. 6 shows a DSC trace of the Reference Form A polymorph.

The DSC analysis confirmed the presence of the polymorph of the invention with a melting point of 120° C. and Reference Form A with a melting point of 133° C. A DSC trace of the polymorph of the invention is shown in FIG. 3, with a DSC of the Reference Form A in FIG. 6.

3. Stability of Polymorphs

Equal amounts of the polymorph of the invention and the Reference Form A polymorph were stirred in 33% methylcyclohexane/xylene for 4 days at a range of temperatures: 6° C., 35° C., 40° C. and 52° C. After the 4 days, the crystals were isolated and dried and their polymorphic form determined by high throughput pXRD.

Powder XRD patterns of the crystals isolated from experiments run at all temperatures showed that the reflections characteristic of Reference Form A were absent.

It can be seen, therefore, that the polymorph of the invention is the stable form over the temperature range studied. As such, formulations of the polymorph of the invention made and stored at up to 52° C. will be unlikely to show unwanted crystal growth.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A method, comprising:
dissolving a compound of formula I,

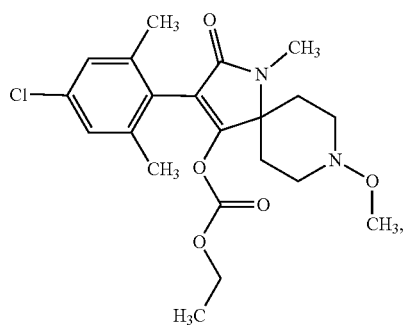

in a methylcyclohexane containing solution;
crystallizing the dissolved compound of formula I.

2. The method of claim 1, further comprising heating the methylcyclohexane until no solid of the compound of formula I remains.

3. The method of claim 2, wherein the heating is to about 85 to 90° C.

4. The method of claim 1, wherein the crystallizing is at room temperature.

5. The method of claim 1, wherein the crystalized compound of formula I has a powder X-ray diffraction pattern comprising one 2θ angle value at 9.4±0.2, one 2θ angle value at 10.3±0.2 and at least three 2θ angle values selected from the group consisting of 8.1±0.2, 11.6±0.2, 12.0±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2.

6. The method of claim 1, wherein the crystalized compound of formula I has lattice parameters: a=8.85 Å±0.01 Å, b=11.43 Å±0.01 Å, c=11.96 Å±0.01 Å, α=65.26°±0.01°, β=77.82°±0.01°, γ=72.60°±0.01° and volume=1043 Å³±1 Å³.

7. The method of claim 1, wherein the crystalized compound of formula I has a powder X-ray diffraction pattern comprises at least six 2θ angle values selected from the group consisting of 8.1±0.2, 11.6±0.2, 12.0±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2.

8. The method of claim 1, wherein the crystalized compound of formula I has a powder X-ray diffraction pattern comprises at least nine 2θ angle values selected from the group consisting of 8.1±0.2, 11.6±0,2, 12.0±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2.

9. The method of claim 1, wherein the crystalized compound of formula I has a powder X-ray diffraction pattern comprises at least twelve 2θ angle values selected from the group consisting of 8.1±0.2, 11.6±0.2, 12.0±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2.

10. The method of claim 1, wherein the crystalized compound of formula I has a powder X-ray diffraction pattern comprises at least fifteen 2θ angle values selected from the group consisting of 8.1±0.2, 11.6±0.2, 12.0±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2.

11. The method of claim 1, wherein the crystalized compound of formula I has a powder X-ray diffraction pattern comprises 2θ angle values selected from 8.1±0.2, 11.6±0.2, 12.0±0.2, 13.9±0.2, 14.8±0.2, 16.0±0.2, 18.2±0.2, 18.8±0.2, 20.4±0.2, 20.6±0.2, 21.2±0.2, 21.7±0.2, 21.9±0.2, 22.1±0.2, 22.4±0.2, and 23.4±0.2.

12. The method of claim 11, wherein the crystalized compound of formula I bas the following lattice parameters: a=8.85 Å±0.01 Å, b=11.43 Å±0.01 Å, c=11.96 Å±0.01 Å, α=65.26°±0.01°, β=77.82°±0.01°, γ=72.60°±0.01° and volume=1043 Å³±1 Å³.

13. The method of claim 1, wherein the crystalized compound of formula I has a melting point of between 120° C.±2° C.

* * * * *